US006866640B2

(12) United States Patent
Francavilla et al.

(10) Patent No.: US 6,866,640 B2
(45) Date of Patent: Mar. 15, 2005

(54) ADAPTOR FOR USE WITH POINT-OF-CARE TESTING CARTRIDGE

(75) Inventors: Frank Francavilla, Newton, NJ (US); Jamieson William Maclean Crawford, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 186 days.

(21) Appl. No.: 10/106,939

(22) Filed: Mar. 26, 2002

(65) Prior Publication Data

US 2002/0143273 A1 Oct. 3, 2002

Related U.S. Application Data

(60) Provisional application No. 60/280,402, filed on Mar. 30, 2001.

(51) Int. Cl.$^7$ ............................ A61B 5/00; B65D 81/00

(52) U.S. Cl. ...................................................... 600/573

(58) Field of Search ................................ 600/573–576; 422/934–936, 939–948; 222/165, 576; 604/187, 276

(56) References Cited

U.S. PATENT DOCUMENTS 2,561,339 A * 7/1951 Alejandro ................... 422/102
4,462,511 A * 7/1984 Fulmer et al. .............. 422/261
4,466,445 A * 8/1984 Abrams ...................... 600/549
4,678,579 A * 7/1987 Griffin ........................ 600/573
5,096,669 A 3/1992 Lauks et al.
5,388,392 A 2/1995 Linnecke
5,611,785 A 3/1997 Mito et al.
5,638,828 A 6/1997 Lauks et al.
5,766,136 A * 6/1998 Cawood ..................... 600/573
5,779,650 A 7/1998 Lauks et al.
6,010,463 A 1/2000 Lauks et al.
6,027,482 A 2/2000 Imbert
6,213,597 B1 4/2001 Liu
6,350,254 B1 2/2002 Wilkinson et al.
6,610,034 B1 * 8/2003 Fischer et al. .............. 604/241

FOREIGN PATENT DOCUMENTS

EP 0 743 095 A1 11/1996

* cited by examiner

*Primary Examiner*—Max F. Hindenburg
*Assistant Examiner*—Brian Szmal

(57) ABSTRACT

An adaptor is provided to facilitate delivery of a fluid specimen from a syringe to a point-of-care testing cartridge. The adaptor includes a tube with an outlet end, an inlet end and a passage extending between the ends. The outlet end of the tube is dimensioned for mating with the entry port of the testing cartridge. The inlet end of the tube is dimensioned for mating with the syringe. The adaptor further includes a support wall extending transversely from the tube and at least one positioning wall extending from the support wall. The positioning wall is spaced transversely from the outlet of the tube by a distance substantially equal to the distance between a side wall of the testing cartridge and the entry port of the testing cartridge. A bottom wall and a lock arm extend from the positioning wall. The bottom wall of the adaptor engages the bottom wall of the testing cartridge and the lock arm of the adaptor engages the top wall of the testing cartridge.

10 Claims, 9 Drawing Sheets

ADAPTOR FOR USE WITH POINT-OF-CARE TESTING CARTRIDGE

RELATED APPLICATIONS

This application claims priority on U.S. Provisional Patent Appl. No. 60/280,402 filed on Mar. 30, 2001.

BACKGROUND OF THE INVENTION

1. Field of the Invention

The subject invention relates to an adaptor to enable precise delivery of small drops of a specimen from a syringe to a point-of-care testing cartridge.

2. Description of the Related Art

Many medical procedures require diagnostic tests to be performed on a sample of a patient's fluid. Fluid often is collected from a patient by employing a needle holder assembly and one or more evacuated tubes. Fluid also can be collected in a syringe. A syringe may be used with a metallic needle to obtain a fluid sample from a patient. However, syringes often are connected directly to an established arterial or venous line to obtain a fluid sample. The fluid collected in the syringe then may be transferred to a tube. The tubes are labeled carefully and shipped to a laboratory for analysis. The results of the laboratory analysis then are reported back to the health care provider. The results, of course, could be rushed in emergency situations, but absent an emergency would require more then one day between the time the sample is drawn from the patient to the time that the laboratory analysis is reported to the health care provider.

Devices have been developed for performing at least certain diagnostic tests on a sample of fluid at the point-of-care. The point-of-care diagnostic equipment includes a syringe for receiving a sample of fluid from a patient, a small disposable testing cartridge for receiving a portion of the fluid from the syringe and a portable clinical analyzer for analyzing the fluid and outputting the results. Combinations of testing cartridges and portable clinical analyzers are marketed in the United States by i-STAT Corporation, AVL Scientific Corporation and Diametrics Medical, Inc. The systems produced by these and other companies share certain common features. In particular, the testing cartridge of each system typically has a small rectangular housing about 1"×2" and about 0.25" thick. The housing includes an internal reservoir with a volume of between about 40 $\mu$l and 125 $\mu$l. An inlet port extends through an external wall of the testing cartridge and communicates with the internal reservoir. The cartridge further includes contact pads and sensors that can be placed in communication with the portable clinical analyzer. An example of an i-STAT point-of-care testing cartridge is shown in U.S. Pat. No. 5,638,828.

The prior art point-of-care testing systems are employed with a syringe that is used to draw a sample of fluid from a patient. The syringe then may be used to eject a portion of the fluid sample into the inlet port of the point-of-care testing cartridge. However, some testing cartridges are operative to automatically draw fluid from the syringe. The inlet port of the cartridge then is closed and the cartridge is placed in communication with the portable clinical analyzer for performing certain specified diagnostic tests on the sample of fluid in the cartridge. The analyzer then provides a very quick output of the test results without the need for sending the fluid sample to the laboratory.

Point-of-care testing systems provide several efficiencies over systems that require virtually all diagnostic tests to be performed at a location remote from the point-of-care. The small size of the testing cartridge facilitates storage and shipment of the cartridges while also contributing to the portability of the system. However, with regards to transferring a collected sample to the cartridge, the small cartridges can be very difficult to use. For example, alignment of the distal end of the syringe with the inlet port of the testing cartridge can be complicated and difficult. A misalignment or imprecise mating of the syringe with the inlet port of the testing cartridge can lead to a loss of a portion of the collected fluid sample. Additionally, it is difficult to use a syringe for accurately dispensing the proper volume of liquid. Too small a volume may prevent proper testing by the cartridge and the associated portable clinical analyzer. Too large a volume can cause splattering or spillage. Similarly an overfill can result in splatter when the cover of the point-of-care testing cartridge is closed. Fluid that is not delivered efficiently from the syringe into the inlet port of the testing cartridge create the potential for disease transmission. Similarly, a loss of fluid during the transfer from the syringe to the testing cartridge can leave an insufficient volume of fluid for performing the required diagnostic tests. An insufficient volume of fluid to perform the required tests can require the health care worker to return to the patient for a second sample of fluid. This is time consuming for the health care worker and traumatic for the patient. Additionally, some testing cartridges may require an insufficiently filled cartridge to be discarded and a new cartridge to be employed with the new sample of fluid. Thus, inefficiencies in the transfer of fluid from the syringe to the testing cartridge can generate excess costs for additional testing cartridges.

The direct transfer of fluid from a syringe to a testing cartridge can cause the syringe tip to close off the entry port and prevent venting of air from the testing cartridge. Thus bubbles are created. Bubbles reduce the volume of fluid and can affect test results.

SUMMARY OF THE INVENTION

The subject invention is directed to an adaptor to enable precise delivery of small drops of a specimen from a syringe assembly to a point-of-care testing cartridge. The point-of-care testing cartridge may be a prior art testing cartridge as described above, or any yet-to-be developed testing cartridge for performing point-of-care diagnostic analysis on a collected specimen of blood or other bodily fluid. The testing cartridge comprises a housing having an internal reservoir for receiving a specimen to be tested. The housing may be substantially rectangular, with opposed top and bottom walls and a plurality of side walls. An entry port extends through the top wall and that communicates with the internal reservoir of the testing cartridge. The testing cartridge may further include contact pads and sensors that can be placed in communication with a portable clinical analyzer for performing point-of-care analysis of the collected specimen.

The syringe assembly that is used with the adaptor may be a conventional prior art syringe assembly. The syringe assembly includes a body with opposed proximal and distal ends. A barrel extends distally from the proximal end of the body and defines a fluid receiving chamber that is widely open at the proximal end. A Luer tip projects from the barrel to the distal end of the syringe body and includes a passage that communicates with the fluid receiving chamber. The Luer tip includes a conically tapered outer surface that is dimensioned and configured for mating with the tapered proximal entry to the hub of a needle assembly or with the base of a plastic Luer fitting or a blunt plastic cannula. The distal end of the syringe body may further have an internally threaded Luer collar that projects from the distal end of the barrel and concentrically around the Luer tip. The threads of the Luer collar can be threadedly engaged with lugs at the proximal end of the hub of a needle assembly or with comparable lugs at the proximal end of a plastic Luer fitting or blunt plastic cannula. Luer tips, Luer collars and mating structures on needles or cannulas are known in the art.

The syringe assembly further includes a plunger that is slidably received in the open proximal end of the fluid receiving chamber defined by the syringe barrel. Distal movement of the plunger in the fluid receiving chamber will expel a fluid from the chamber and through the Luer tip. Proximal movement of the plunger in the chamber will draw fluid through the Luer tip and into the chamber.

The syringe assembly with which the adaptor is used may further include a needle assembly, a plastic Luer fitting or a blunt plastic cannula for accessing blood or other bodily fluid to be tested. A conventional prior art needle assembly includes an elongate metallic needle cannula having a proximal end, a pointed distal end and a lumen extending between the ends. The prior art needle assembly farther includes the plastic hub having opposed proximal and distal ends. The distal end of the hub is securely mounted to the proximal end of the needle cannula. The proximal end of the hub is configured for fluid-tight engagement with the Luer tip. Additionally, the proximal end of the hub may include lugs for threaded engagement with the internal threads on a Luer collar that may be present on the syringe. A Luer fitting or blunt plastic cannula typically is unitarily molded from a plastic material and has opposite proximal and distal ends and a lumen extending between the ends. The proximal end of the blunt plastic cannula may have the same shape as the proximal end of the hub for the above-described needle assembly. The distal end of the blunt plastic cannula may be tapered sufficiently to pierce a septum across a fitting on an IV access system or blood collection set.

The adaptor of the subject invention may be unitarily molded from a plastic material and comprises a tapered tube with a cross-sectionally small outlet section for aligning with the entry port of the prior art testing cartridge, a cross-sectionally large inlet section for mating with the Luer tip of the syringe and a passage or lumen extending between the inlet and outlet sections. Portions of the passage or lumen in the outlet section of the tapered tube define a cross-sectionally small bore to minimize drop size and to provide a highly controlled and easy fill of the specimen into the reservoir of the testing cartridge. Thus, the small bore outlet section of the tapered tube functions essentially in the manner of an eye dropper to deliver the specimen to the testing cartridge one drop at a time. Thus, overfill and spillage substantially can be avoided.

The adaptor further includes a cantilevered support wall extending unitarily from the outlet section of the tapered tube at a location spaced slightly from the extreme outlet end of the outlet section. The cantilevered support wall may be substantially parallel to the axis of the tube or may pass substantially through the axis of the tube.

A first positioning wall extends unitarily from an end of the cantilevered support wall remote from the tapered tube. The first positioning wall may be aligned substantially parallel to the outlet section of the tapered tube and is spaced from the outlet end of the tapered tube by a distance substantially equal to the distance between the inlet port of the testing cartridge and a side wall of the testing cartridge housing. The adaptor may further include a second positioning wall extending unitarily from the first positioning wall and substantially orthogonal to the first positioning wall. Thus, the second positioning wall also may be substantially parallel to the outlet end of the tapered tube. Additionally, the second positioning wall is spaced from the outlet end of the tapered tube by a distance approximately equal to the offset between the inlet port of the testing cartridge and a second side wall or end wall of the testing cartridge. A bottom wall may extend orthogonally from the positioning walls and may be aligned substantially perpendicular to the outlet end of the tapered tube. The bottom wall is spaced from the outlet end of the tapered tube by a distance to permit the outlet end of the tapered tube to be spaced slightly above the entry port of the testing cartridge when the bottom wall is in sliding engagement with the bottom wall of the testing cartridge. Thus, the bottom wall and the first and second positioning walls ensure proper positioning and alignment of the outlet end of the tapered tube of the adaptor relative to the entry port of the testing cartridge.

The adaptor may further include a lock arm that projects unitarily from the first positioning wall substantially parallel to and spaced from both the second positioning wall and the bottom wall. Thus, the lock arm extends substantially orthogonal to the outlet end of the tapered tube. The lock arm is configured to snap into engagement with portions of the top wall of the testing cartridge in proximity to the entry port. For this purpose, the lock arm may include a detent or projection at the end thereof remote from the first positioning wall to lockingly engage corresponding structure on the top wall of the testing cartridge.

The adaptor can be used by first drawing a specimen of blood or other bodily fluid with a syringe assembly substantially in a conventional manner. For example, the Luer tip of the syringe body, the plastic Luer fitting or the blunt plastic cannula mounted to the Luer tip may be placed in communication with the fitting of an IV access system or blood collection set. Alternatively, a conventional needle assembly may be mounted to the Luer tip of the syringe body and the distal tip of the needle cannula can be inserted into a blood vessel of the patient to obtain the required specimen. With either of these approaches, blood is drawn through the passage of the Luer tip and into the fluid receiving chamber of the syringe body by pulling the plunger of the syringe assembly in a proximal direction. Most point-of-care testing cartridges require between 40 $\mu$l and 125 $\mu$l to complete a test. Hence, the plunger of the syringe assembly is moved proximally to obtain a volume of fluid slightly in excess of the amount required by the particular testing cartridge that will be employed.

After the appropriate volume of fluid has been collected, the needle assembly, if used, is removed in an accepted safe manner and deposited in a sharps receptacle. Alternatively, any plastic Luer fitting or blunt plastic cannula that may have been mounted to the distal end of the syringe body is removed and discarded into a sharps receptacle in a conventional accepted safe manner.

The adaptor of the subject invention then is mounted to the distal end of the syringe body. More particularly, the Luer tip of the syringe body may be urged into fluid-tight frictional engagement with the Luer-tapered inlet to the adapter. Alternatively, the syringe body may include a Luer collar with an array of internal threads and the inlet of the adaptor may include a mating pair of Luer lugs. In this situation, the adaptor is threaded into engagement with the Luer collar while simultaneously urging the Luer tip of the syringe into fluid-tight engagement with the tapered entry to the inlet of the adaptor.

The point-of-care testing cartridge then is removed from the manufacturer's package. Many manufacturers of testing cartridges provide a cover for the inlet port that is hinged into a covering disposition over the inlet port both prior to and after deposition of fluid sample into the testing cartridge. Thus, a cover, if present on the testing cartridge, must be rotated away from the inlet port of the testing cartridge. The syringe assembly and the adaptor are aligned substantially perpendicular to the top wall of the testing cartridge and near the corner of the testing cartridge that has the entry port. The syringe assembly and adaptor then are moved toward the testing cartridge by sliding the bottom wall of the adaptor along the bottom wall of the testing cartridge and by sliding the second positioning wall of the adaptor along the end wall of the testing cartridge. Thus, the outlet section of the tapered tube and the first positioning wall will move toward the entry port and the side wall of the testing cartridge. Sufficient movement will cause the lock arm to deflect slightly and ride over portions of the top wall of the testing cartridge. The lock arm then will snap into engagement with structure on the top wall of the testing cartridge when the first positioning wall of the adaptor engages the side wall of the testing cartridge and when the outlet end of the tapered tube is aligned with and positioned slightly above the entry port to the testing cartridge. The walls and the lock arm of the adaptor hold the adaptor and the syringe in a stable orientation relative to the testing cartridge. The plunger of the syringe assembly then is moved distally to urge a selected volume of the specimen drop-by-drop from the fluid receiving chamber of the syringe body, through the adaptor and into the entry port of the testing cartridge. This operation can be performed one-handed, thereby providing further conveniences and efficiencies. The syringe assembly and the adaptor then may be removed from the testing cartridge and discarded in a conventional safe manner. Simultaneously, the cover of the testing cartridge is rotated over the inlet port of the testing cartridge, and the testing cartridge is presented to a portable clinical analyzer substantially in the conventional manner. Alternatively the testing cartridge may be mounted to the portable clinical analyzer prior to depositing the specimen in the testing cartridge.

DETAILED DESCRIPTION

An adaptor in accordance with the subject invention is identified generally by the numeral 10 in FIGS. 1–4. Adaptor 10 is used with a syringe assembly 12, as shown most clearly in FIG. 5, and with a point-of-care testing cartridge 14, as shown most clearly in FIG. 6.

Figure 1:
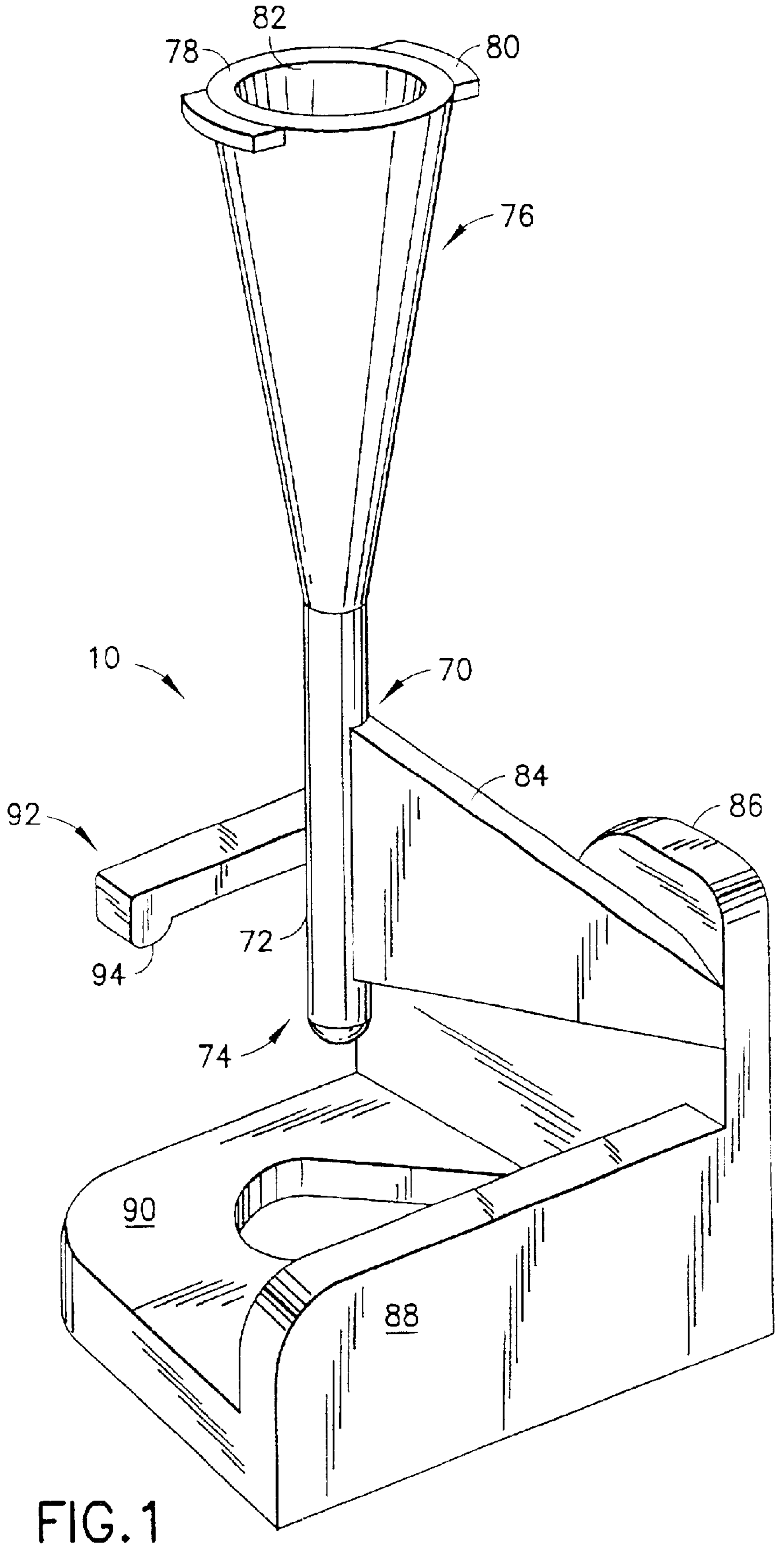
FIG. 1 is a perspective view of an adaptor in accordance with the subject invention.
Figure 2:
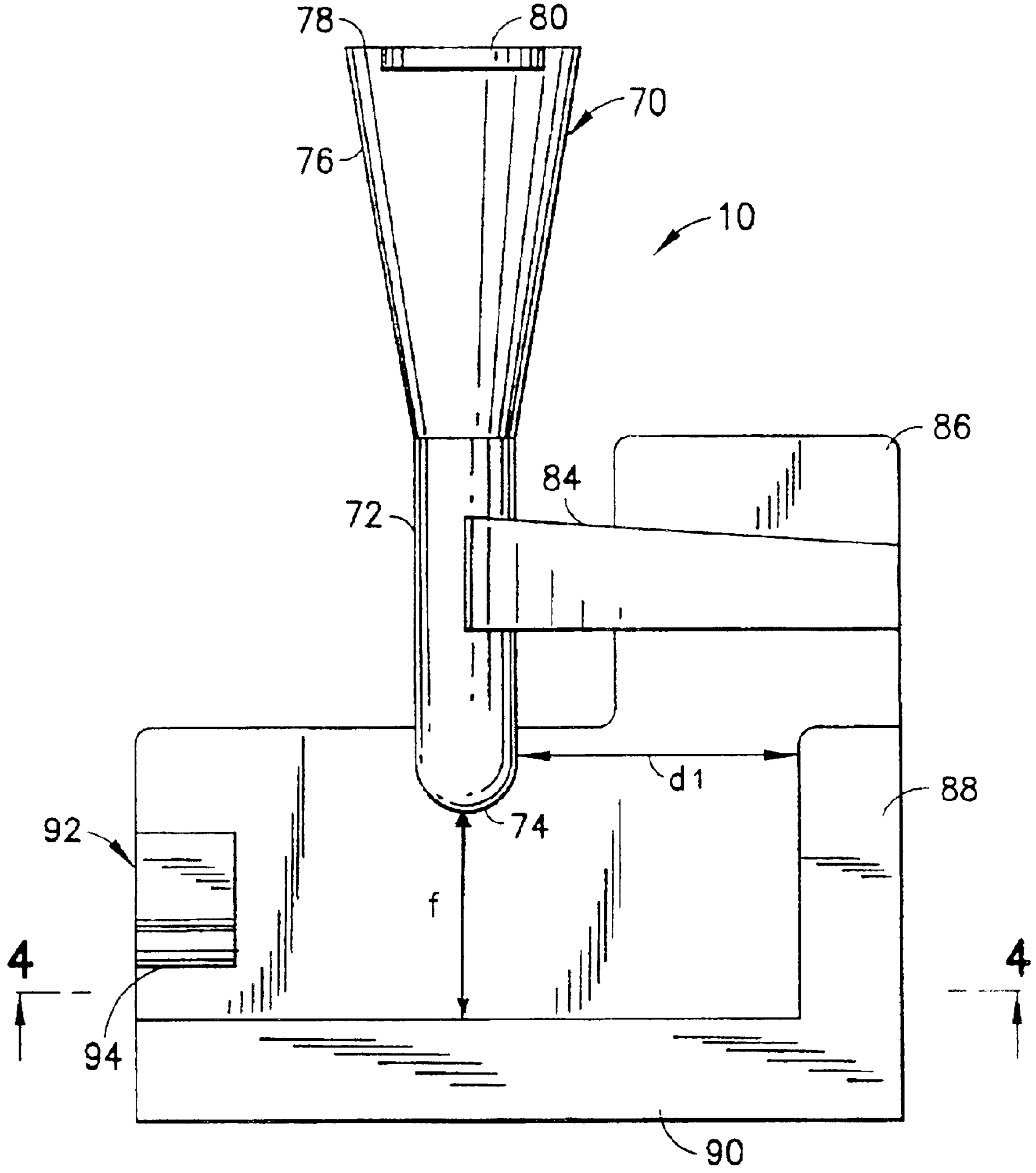
FIG. 2 is a front elevational view of the adaptor.
Figure 3:
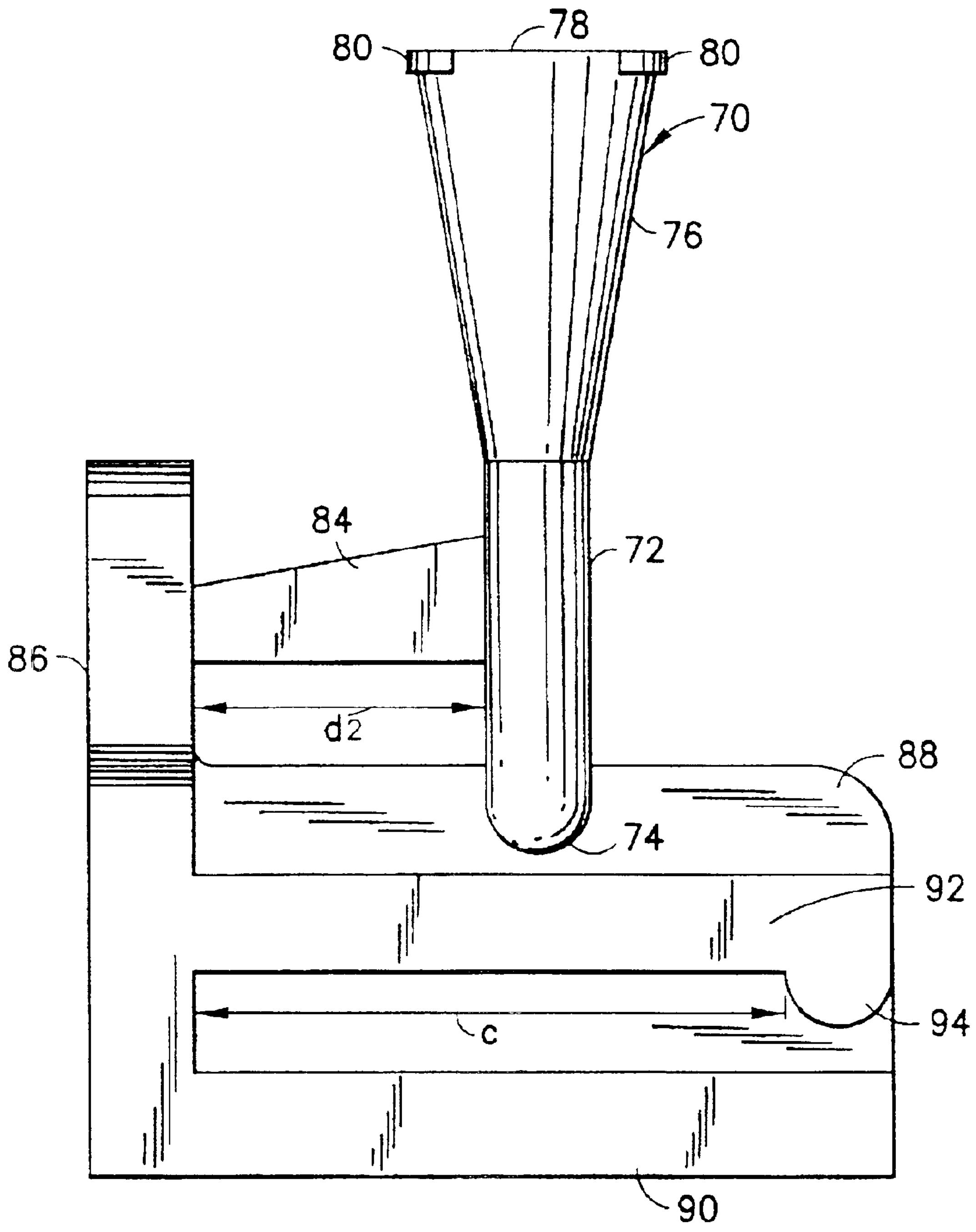
FIG. 3 is a side elevational view of the adaptor.
Figure 4:
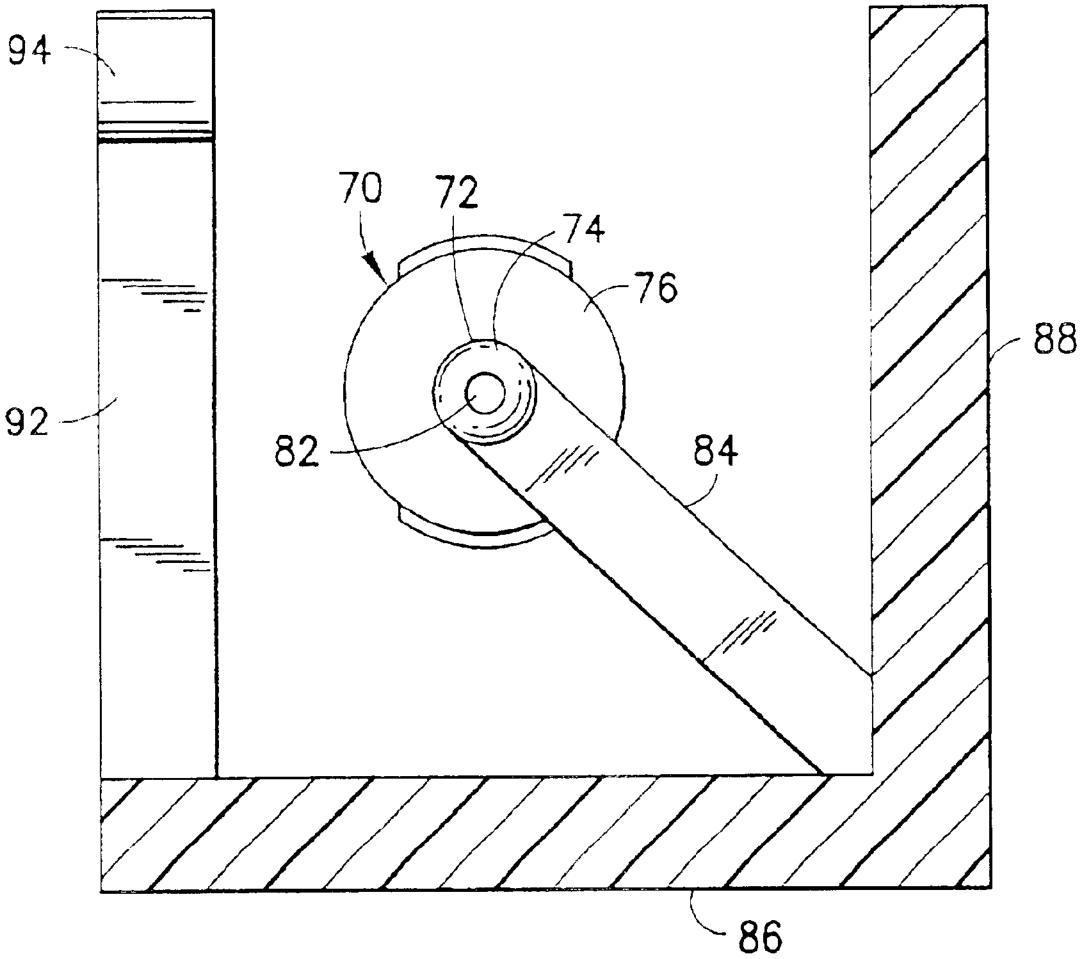
FIG. 4 is a cross-sectional view taken along line 4—4 in FIG. 2.
Figure 5:
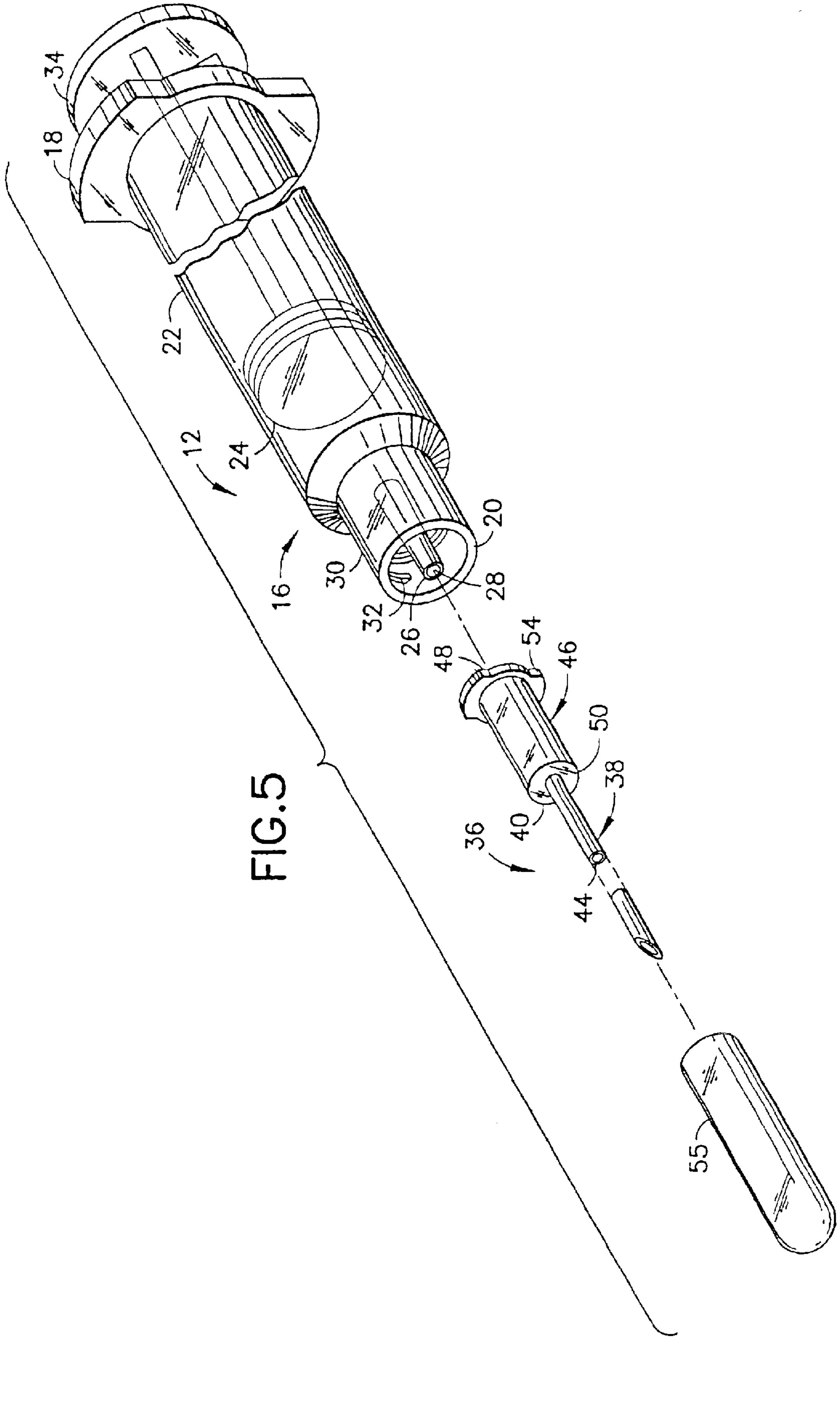
FIG. 5 is a perspective view of a syringe for use with the adaptor shown in FIGS. 1–4.

Syringe assembly 12, as shown in FIG. 5, includes a syringe body 16 having a proximal end 18 and a distal end 20. A barrel 22 extends distally from proximal end 18 and defines a cylindrical fluid receiving chamber 24 that is widely open at proximal end 18. A frustoconically tapered tip 26 extends from barrel 22 to distal end 20 of syringe body 16. Tip 26 is provided with a narrow cylindrical passage 28 that communicates with fluid receiving chamber 24 of barrel 22. An optional Luer collar 30 projects distally from barrel 22 and concentrically surrounds tip 26. Luer collar 30 is provided with an internal array of threads 32. Syringe assembly 12 further includes a plunger 34 slidably disposed in fluid receiving chamber 24 and in fluid-tight engagement with the cylindrical walls of chamber 22. Plunger 34 can be moved alternately in proximal or distal directions for urging fluid through passage 28 in tip 26 and into or out of fluid receiving chamber 24.

Syringe assembly 12 optionally includes a needle assembly 36. Needle assembly 36 includes a metallic needle cannula 38 having a proximal end 40, a sharply pointed distal end 42 and a lumen 44 extending between the ends. Needle assembly 36 further includes a hub 46 that has a proximal end 48, a distal end 50 and a passage extending therebetween. Distal end 50 of hub 46 is securely mounted to proximal end 40 of needle cannula 38 such that the passage through hub 46 communicates with lumen 44 through needle cannula 38. The passage of hub 46 defines a taper that substantially matches tapered distal tip 26 on syringe body 16. Thus, tapered tip 26 of syringe body 16 can be placed in fluid-tight frictional engagement with the passage in proximal end 48 of hub 46. Proximal end 48 of hub 46 is further characterized by a pair of diametrically opposite lugs 54 that are dimensioned and configured for engagement with threads 32 of Luer collar 30. Thus, lumen 44 through needle cannula 38 can be placed in communication with passage 28 in tip 26 and with fluid receiving chamber 24 of syringe body 16. Needle assembly 36 further includes a protective cap 55 removably engaged over needle cannula 38.

Figure 6:
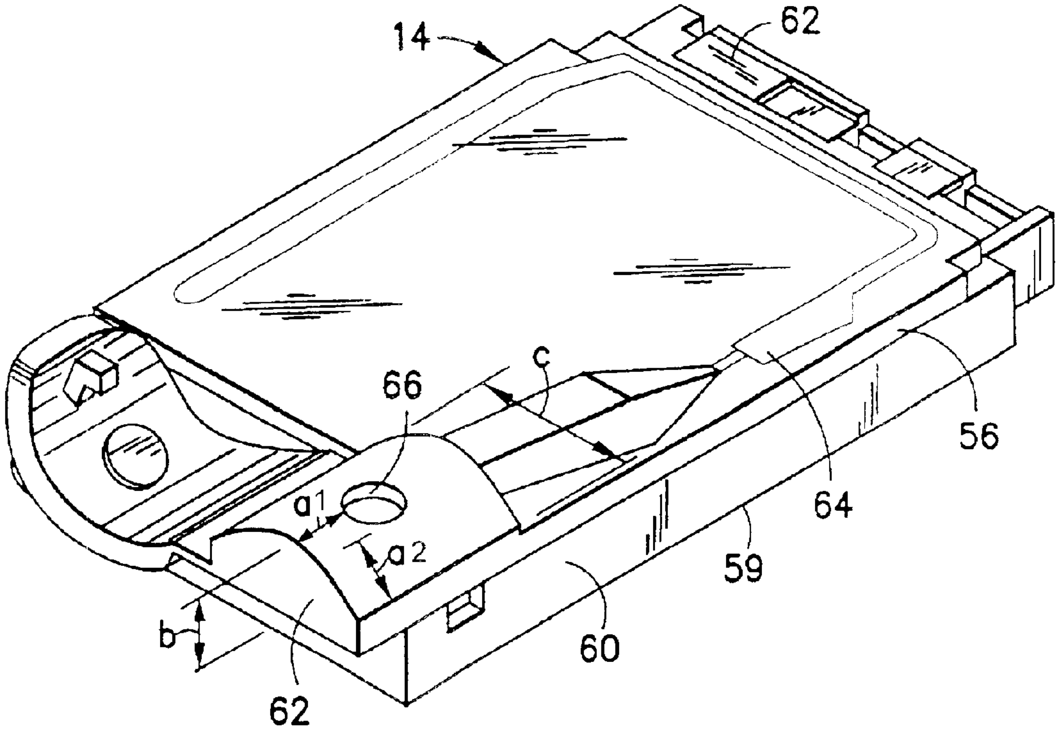
FIG. 6 is a perspective view of a testing cartridge for use with the adaptor.
Figure 7:
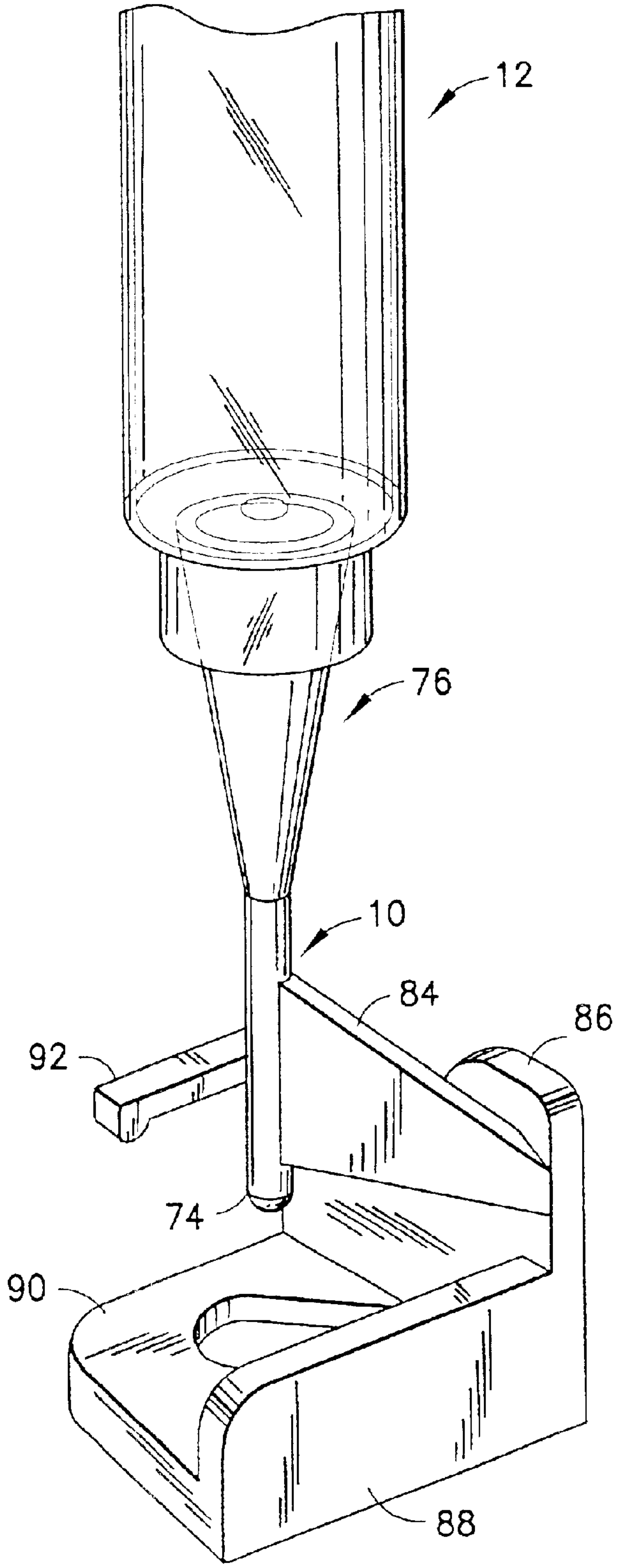
FIG. 7 is a perspective view of the adaptor mounted to the syringe.
Figure 8:
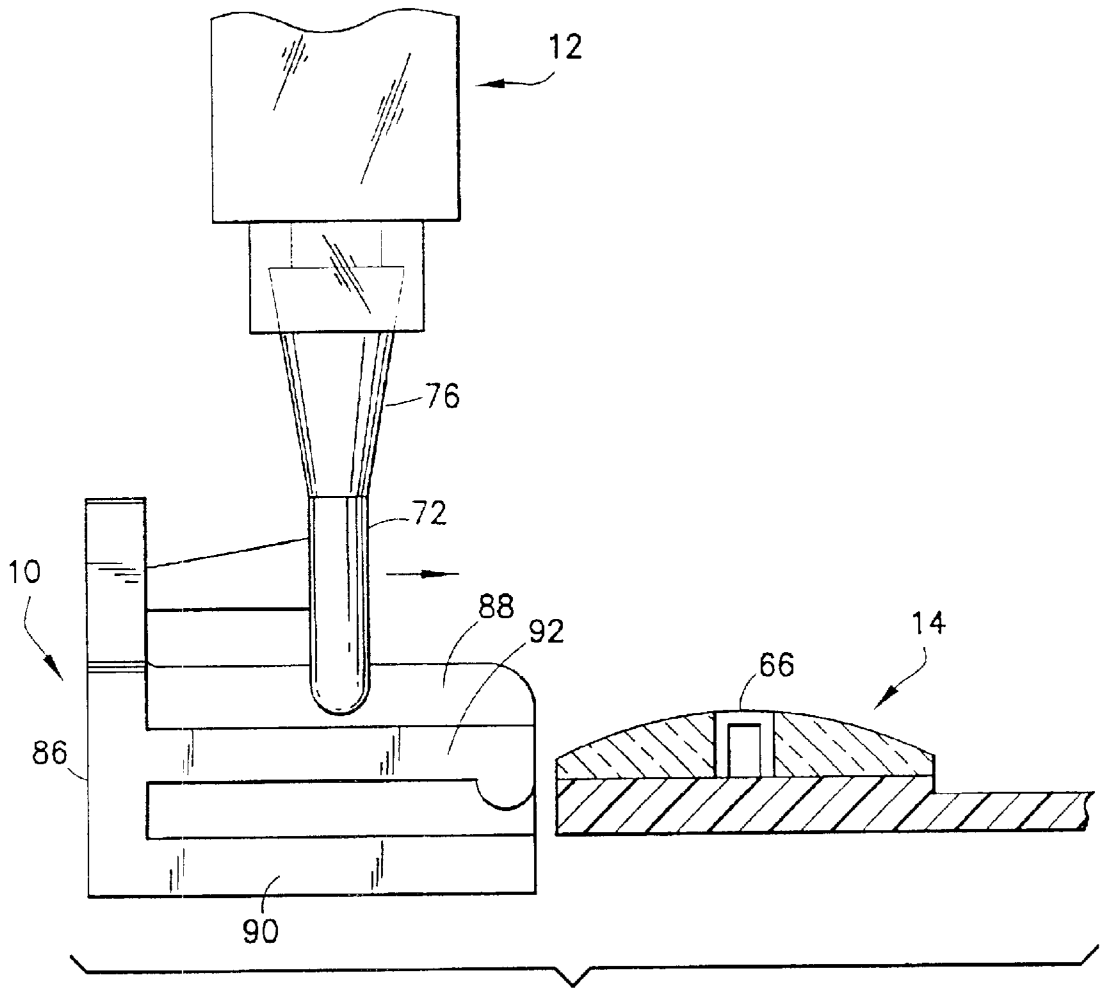
FIG. 8 is a cross-sectional view showing the adaptor and syringe guided toward the inlet port of the testing cartridge.
Figure 9:
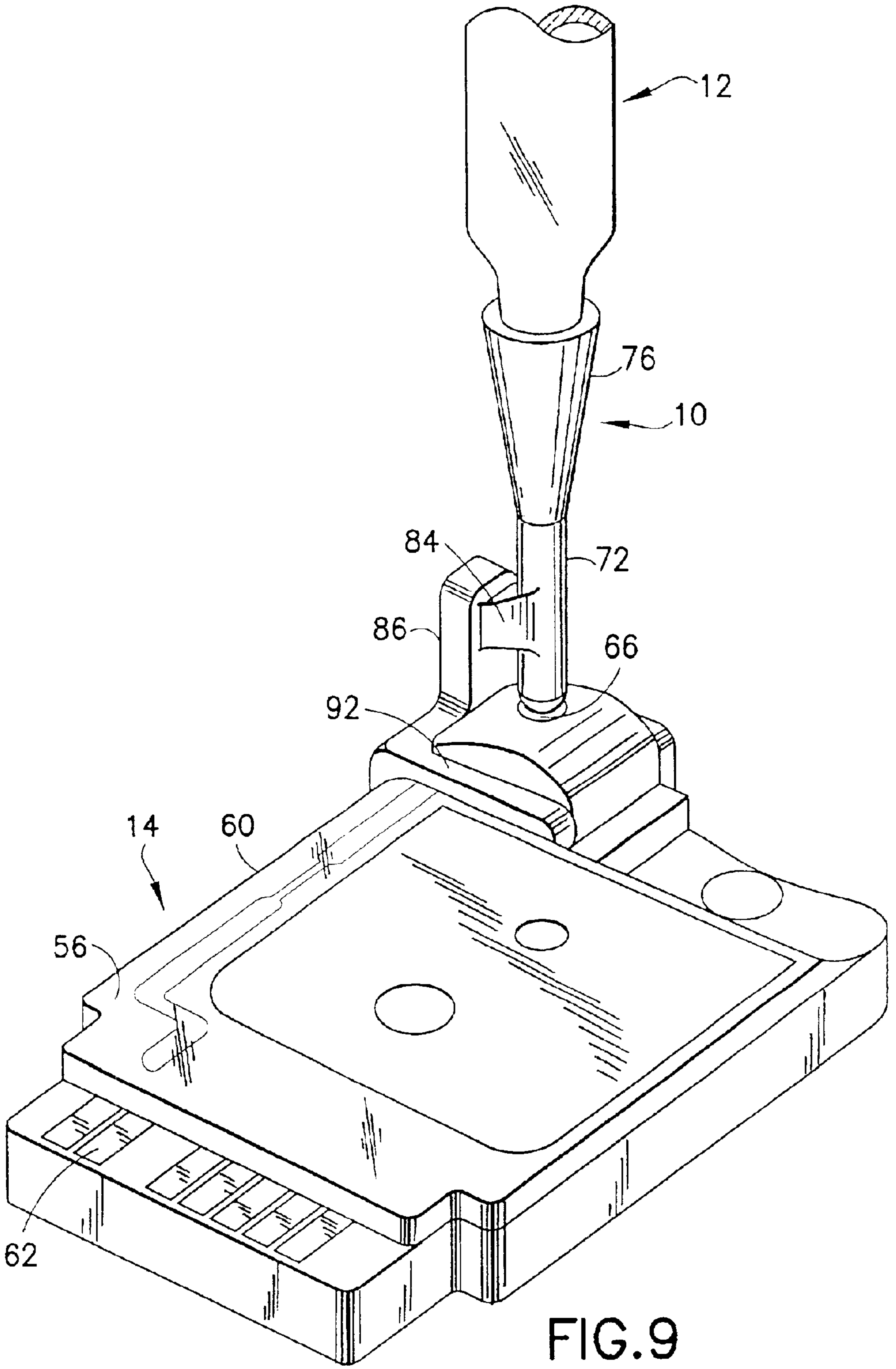
FIG. 9 is a perspective view showing the adaptor and syringe fully mounted on the testing cartridge for delivering a specimen to the testing cartridge.

Point-of-care testing cartridge 14 is shown in FIG. 6 and may be of any of several prior art designs, including those manufactured by i-STAT Corporation, Diametrics Medical, Inc., AVL Scientific Corporation or any other such testing cartridges that are available or become available. One such testing cartridge is disclosed in U.S. Pat. No. 5,638,828, the disclosure of which is incorporated herein by reference.

Testing cartridge 14 includes a generally rectangular body 56 with opposed top and bottom walls 58 and 59 that define a length of approximately 1.5–2.0 inches and a width of about 1.0 inches. Body 56 further has side walls 60 and end walls 62 that define a thickness for body 56 of about 0.25 inches. A fluid reservoir 64 is formed inside body 56 of cartridge 14 and has a volume in the range of 40 $\mu$l and 125 $\mu$l. Body 56 further includes an entry port 66 that extends through top wall 58 and communicates with reservoir 64. Entry port 66 is slightly tapered from a relatively large diameter portion externally on housing 56 to a relatively smaller cross-section closer to reservoir 58. Additionally entry port 66 is spaced from one side wall 60 and one end wall 62 by distances a1 and a2. Additionally, portions of top wall 58 at entry port 66 are spaced from bottom wall 59 by a distance b. Furthermore, portions of top wall in proximity to entry port 66 define a convex cylindrical arc generated about an axis that extends parallel to side wall 60. A recess 67 is formed in top wall 58 at a location spaced distance c from side wall 60. Testing cartridge 14 further includes contact pads and sensors 68 that can be placed in communication with a portable clinical analyzer for performing various point-of-care diagnostic tests on the sample of blood in the reservoir 64 and for providing various readout data that can be used by a health care technician at the point-of-care and/or at a remote location.

Adaptor 10 is unitarily molded from a plastic material and includes a tapered tube 70. Tube 70 includes a narrow cylindrical outlet section 72 with a slightly rounded or tapered outlet end 74. Tube 70 further includes a substantially tapered female Luer fitting 76 that is substantially concentric with outlet section 72. Luer fitting 76 includes an inlet end 78 with a pair of diametrically opposite Luer lugs 80 that are dimensioned and configured for threaded engagement with threads 32 on Luer collar 30 of syringe assembly 12. However, not all syringes include a Luer collar, and an adaptor for use with syringes that have no Luer collar need not be provided with lugs 80. Tapered tube 70 further includes a passage 82 extending axially from inlet end 78 to outlet end 74. Portions of passage 82 adjacent inlet end 78 are conically tapered for fluid-tight engagement with Luer tip 26 of syringe body 16. Portions of passage 82 adjacent outlet end 74 define a cross-sectionally narrow bore for producing small drops of a specimen directed through passage 82 as explained further below.

Adaptor 10 further includes a cantilevered support wall 84 that extends substantially transverse to tapered tube 70 at a location between inlet end 78 and outlet end 74. More particularly, cantilevered support wall 84 is substantially planar and is parallel to or passes through the axis of tapered tube 70. A first positioning wall 86 extends from an end of cantilevered support wall 84 remote from tapered tube 70. First positioning wall 86 is substantially planar and is aligned substantially parallel to tapered tube 70. First positioning wall 86 and outlet end 74 of tapered tube 70 are spaced from one another by a distance d2 which is approximately equal to or slightly greater than the distance a2 between entry port 66 of testing cartridge 14 and side wall 60 thereof.

A second positioning wall 88 extends orthogonally from first positioning wall 86 and substantially parallel to the axis of tapered tube 70. The second positioning wall 88 also is spaced from outlet end 74 of tapered tube 70 by distance d1 which is equal to or slightly greater than distance a1 between entry port 66 of testing cartridge 14 and end wall 62 thereof.

A bottom wall 90 extends orthogonally from both first and second positioning walls 86 and 88 and is aligned perpendicular to the axis of tapered tube 70. Bottom wall 90 is spaced from outlet end 74 by distance f which is slightly greater than the thickness b of testing cartridges 14 at entry port 66. Thus, as explained further herein, outlet end 74 of tapered tube 70 will be positioned slightly above entry port 66 of testing cartridge 14 when bottom wall 90 of adaptor 10 is positioned against bottom wall 59 of testing cartridge 14.

Adaptor 10 also includes a locking arm 92 that extends from first positioning wall 86. Locking arm 92 is aligned substantially parallel to bottom wall 90 of adaptor 10. Additionally, locking arm 92 is disposed on a side of outlet section 72 of tapered tube 70 opposite from a second positioning wall 88. Locking arm 92 includes a locking detent 94 at a location spaced from first positioning wall 86 by distance c which is substantially identical to the spacing between side wall 60 of testing cartridge 14 and recess 67 thereof.

Syringe assembly 12 is used in a conventional manner to draw a sample of fluid from a patient. More particularly, needle assembly 36 can be mounted to Luer tip 26 of syringe body 16, and needle cannula 38 of needle assembly 36 can be inserted into a blood vessel of a patient or other source of bodily fluid for drawing a sample of blood or other such fluid. Alternatively, a blunt plastic cannula or other plastic Luer fitting can be mounted to Luer tip 26, and the distal end of the blunt plastic cannula or other fitting can be urged through the septum that seals a fitting of a fluid collection set. Still further, syringe assembly 12 can be connected directly to an arterial or venous line that had already been placed in communication with a patient. With any of these optional approaches, plunger 34 is moved proximally after accessing the supply of fluid. Proximal movement of plunger 34 draws fluid into fluid receiving chamber 24 of syringe barrel 22. The volume of fluid drawn into fluid receiving chamber 24 is in excess of the volume of fluid required for testing cartridge 14, which typically is in the range of 40 μl–125 μl. Needle assembly 36 or the blunt plastic cannula, if used, then is removed from syringe body 16 substantially in a conventional manner and is disposed of in a sharps receptacle.

Adaptor 10 then is mounted to Luer tip 26. More particularly, Luer tip 26 is axially aligned with inlet end 78 of Luer fitting 76 of adaptor 10. In the illustrated embodiments, syringe assembly 12 includes a Luer collar 30, and adaptor 10 includes lugs 80 that are dimensioned for engagement with threads 32 of Luer collar 30. Thus, in this embodiment adaptor 10 is rotated for threaded engagement of lugs 80 with threads 32 of Luer collar 30. This threaded engagement causes Luer tip 26 of syringe body 16 to be urged into fluid-tight engagement with conically tapered portions of passage 82 adjacent inlet end 78 of adaptor 10. Other syringes, however, may not have a Luer collar. For these embodiments, adaptor 10 need not have lugs 80 or lugs 80 need not be utilized. Thus, the conically tapered tip of a syringe without a Luer collar can merely be urged axially into fluid-tight frictional engagement with conically tapered surfaces of passage 82 adjacent inlet end 78.

Point-of-care testing cartridge 14 then is removed from the manufacturer's package, and any closure that may have been positioned over entry port 66 is rotated away from entry port 66. Syringe assembly 12 and adaptor 10 then are aligned substantially perpendicular to top and bottom walls 58 and 59 of testing cartridge 14 and in proximity to the corner of testing cartridge 14 closest to entry port 66. Bottom wall 90 of adaptor 10 then is slidably engaged on bottom wall 59 of testing cartridge 14. Simultaneously, second positioning wall 88 is slidably engaged with end wall 62 of testing cartridge 14. Syringe assembly 12 and adaptor 10 then are moved parallel to second positioning wall 88 and bottom wall 90. Sufficient movement will cause locking arm 92 to ride over top wall 58 of testing cartridge 14 and to deflect slightly away from bottom wall 90 of adaptor 10. This movement causes first positioning wall 86 to approach sidewall 60 of testing cartridge 14. Detent 94 on locking arm 92 will align with recess 67 in top wall 58 and will snap into engagement with recess 67. The locked engagement of detent 94 with recess 67 will occur substantially when first positioning wall 86 abuts side wall 60 of testing cartridge 14 and when outlet end 74 of tapered tube 70 registers with entry port 66. Thus, adaptor 10 and syringe assembly 12 will be stably engaged with testing cartridge 14 such that outlet end 74 of adaptor 10 will be aligned for efficient delivery of small droplets of specimen from syringe assembly 12 to entry port 66.

The use of testing cartridge 14 proceeds merely by urging plunger 34 distally in syringe body 16. Movement of plunger

34 causes fluid in fluid receiving chamber 24 to be urged through Luer tip 26 of syringe body 16, through passage 82 of adaptor 10 and drop-by-drop into reservoir 64 of testing cartridge 14. Syringe assembly 12 and adaptor 10 then are separated from testing cartridge 14. The cover of testing cartridge 14 then is rotated into the closed position and syringe assembly 12 and adaptor 10 are discarded in a safe accepted manner.

What is claimed is:

1. An adaptor for use with a testing cartridge and a syringe to facilitate delivery of a fluid specimen from said syringe to said testing cartridge, said testing cartridge having a housing with top and bottom walls defining a thickness for said testing cartridge, said testing cartridge further having a pair of opposed side walls and a pair of opposed end walls extending between said too and bottom walls, said entry port of said testing cartridge extending through said top wall at a first distance from one said side wall and at a second distance from one said end wall, said adaptor comprising: a bottom wall, a positioning wall extending angularly from said bottom wall, a support wall cantilevered from said positioning wall and spaced from said bottom wall, a tapered tube connected to said support wall at a location spaced from said positioning wall, said tapered tube having an outlet end, an inlet end and a passage extending between said ends, said outlet end being spaced from said bottom wall, of said adaptor by a distance greater than the thickness of said testing cartridge and being spaced from said positioning wall by a distance substantially equal to said first distance, whereby said outlet end of said tapered tube substantially aligns with said entry port of said testing cartridge when said bottom wall and said positioning wall of said adaptor are engaged with said bottom wall and said side wall of said testing cartridge.

2. The adaptor of claim 1, wherein said positioning wall is a first positioning wall, and wherein said adaptor further comprises a second positioning wall connected to said bottom wall and spaced from said outlet end of said tube by a distance substantially equal to said second distance.

3. The adaptor of claim 1, further comprising a lock arm extending from said positioning wall and configured for locked engagement with said top wall of said testing cartridge when said outlet end of said tube is aligned with said entry port of said testing cartridge.

4. The adaptor of claim 1, wherein said adaptor is a formed of plastic, and wherein said bottom wall, said positioning wall, said support wall and said tapered tube are unitary with one another.

5. The adaptor of claim 1, wherein said bottom wall of said adaptor is substantially perpendicular to said positioning walls and to said tube.

6. The adaptor of claim 1, wherein said inlet of said tube of said adaptor is tapered.

7. The adaptor of claim 6, wherein said inlet of the tube of said adaptor comprising a pair of opposite Luer projections for threaded engagement with a Luer collar.

8. An adaptor for a testing cartridge, said adaptor comprising a bottom wall, first and second positioning walls angularly aligned to one another and projecting rigidly and unitarily from the bottom wall, a support wall cantilevered rigidly and unitarily from said first positioning wall and a tapered tube extending rigidly and unitarily from an end of said support wall spaced from said first and second positioning walls, said tapered tube being aligned substantially perpendicular to said bottom wall and being spaced from said bottom wall, said tapered tube having an outlet end substantially opposed to said bottom wall, and inlet end and a passage extending between said ends, said inlet end defining a Luer taper, whereby said inlet end of said tapered tube of said adaptor is releasably engageable with a Luer fitting of a syringe for delivering a liquid specimen to a point-of-care testing cartridge supported on said bottom wall of said adaptor.

9. The adaptor of claim 8, wherein said first and second positioning walls are substantially perpendicular to one another and are unitary with one another.

10. The adaptor of claim 9, further comprising a lock arm cantilevered from said first positioning wall and aligned substantially parallel to said bottom wall.

* * * * *